United States Patent [19]

Madou et al.

[11] Patent Number: 4,812,221
[45] Date of Patent: Mar. 14, 1989

[54] FAST RESPONSE TIME MICROSENSORS FOR GASEOUS AND VAPOROUS SPECIES

[75] Inventors: Marc J. Madou, Palo Alto; Takaaki Otagawa, Fremont, both of Calif.

[73] Assignee: SRI International, Menlo Park, Calif.

[21] Appl. No.: 73,495

[22] Filed: Jul. 15, 1987

[51] Int. Cl.[4] ............................................. G01N 27/54
[52] U.S. Cl. .................................... 204/412; 414/415; 414/432
[58] Field of Search ............... 204/415, 412, 403, 431, 204/432, 414; 128/635

[56] References Cited

U.S. PATENT DOCUMENTS

| | | | |
|---|---|---|---|
| 4,049,503 | 9/1977 | Becker et al. | 204/1 T |
| 4,062,750 | 12/1977 | Butler | 204/415 |
| 4,076,596 | 2/1978 | Connery et al. | 204/1 T |
| 4,100,048 | 7/1978 | Pompei et al. | 204/415 |
| 4,473,456 | 9/1984 | Hawkins | 204/414 |
| 4,592,824 | 6/1986 | Smith et al. | 204/416 |

Primary Examiner—G. L. Kaplan
Attorney, Agent, or Firm—Fliesler, Dubb, Meyer & Lovejoy

[57] ABSTRACT

The present invention relates to a sensor for gaseous and vaporous species. The sensor comprises a substrate having a surface having an opening therein. A gas and vapor permeable sensing electrode having front and back sides is located across the opening with the front side facing generally the same direction as does the surface. A gas flow path leads to the back side of the sensing electrode. An electrolytic medium is in contact with the front side of the electrode. An additional electrode is in contact with the electrolytic medium and is electronically isolated from the sensing electrode other than via the electrolytic medium. A gas sensor as described has a very fast response time and an extended lifetime and can be made selective for any of a number of different gaseous species.

24 Claims, 3 Drawing Sheets

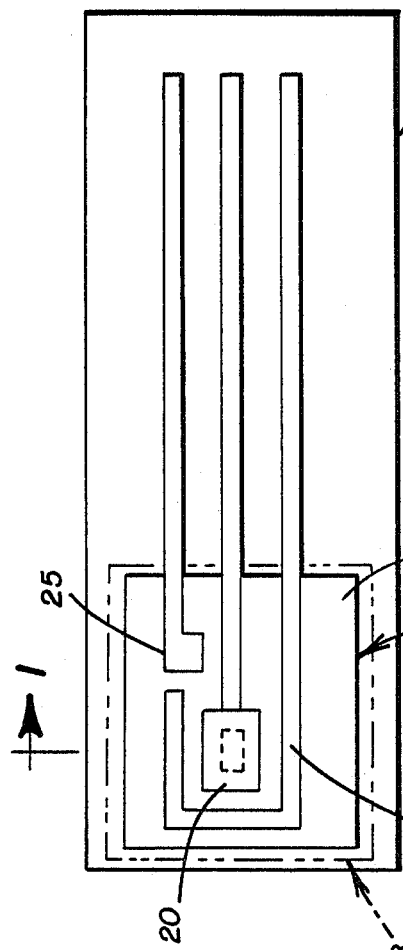
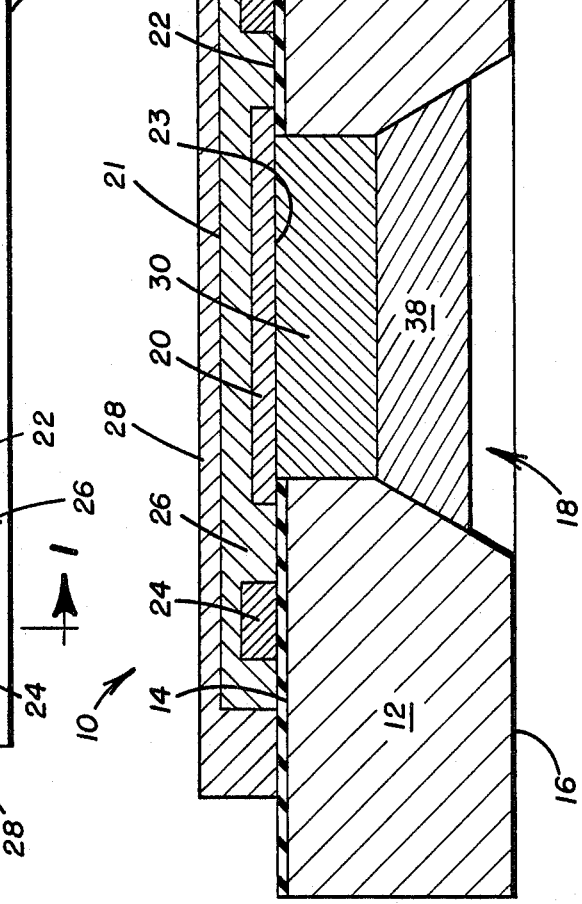

FAST RESPONSE TIME MICROSENSORS FOR GASEOUS AND VAPOROUS SPECIES

TECHNICAL FIELD

The present invention relates to microsensors for gaseous and vaporous species.

BACKGROUND ART

Currently gases such as oxygen can be determined by so-called planar Clark-type sensors wherein a sensing electrode and a reference electrode are deposited on a substrate using conventional semiconductor device fabrication techniques and a hydrogel layer is utilized as the electrolyte. A gas permeable membrane may cover the hydrogel layer and the electrodes. The oxygen to be determined in such a structure must pass through the membrane, dissolve in the hydrogel, pass through the hydrogel, and finally contact the sensing electrode. As a result, the response time of such electrodes is not as fast as might be desired. In fact, even the fastest sensing of this type of sensor, when made on a microscale, has a response time of at least five seconds and often ten seconds or more. Furthermore, such sensors are generally used only to determine oxygen and are not used, generally, for determining the concentrations of a number of gaseous species.

It would be highly desirable to have a faster responding gas sensor, or an array of such sensors, which could be made selectively sensitive to any of a number of different gaseous species.

The present invention is directed to overcoming one or more of the problems as set forth above.

DISCLOSURE OF INVENTION

In accordance with the present invention a sensor for gaseous and vaporous species is set forth. The sensor comprises a substrate having a surface having an opening in it. A gas and vapor permeable sensing electrode having front and back sides is located across the opening with the front side facing generally the same direction as does the surface. A gas flow path is provided leading to the back side of the sensing electrode. An electrolytic medium is in contact with the front side of the sensing electrode. An additional electrode is in contact with the electrolytic medium and is electronically isolated from the sensing electrode other than via the electrolytic medium.

In accordance with another embodiment of the present invention a gas and vapor sensor is set forth comprising a gas and vapor permeable substrate having a surface. Means are provided for making selected portions of the surface gas and vapor impermeable while leaving an area thereof which remains gas and water permeable. A gas and vapor permeable sensing electrode having front and back sides is located across said area with its front side facing generally the same direction as does the surface. An electrolytic medium is in contact with the front side. An additional electrode is in contact with an electrolytic medium and is electronically isolated from the sensing electrode other than via the electrolytic medium.

In accordance with yet another embodiment of the present invention a gas sensor is set forth comprising a substrate having first and second surfaces and having a passage therethrough from the first surface to the second surface. A gas permeable sensing electrode having first surface and second surface sides is positioned across the passage. An electrolytic medium is in contact with the first surface side of the electrode. An additional electrode is in contact with the electrolytic medium and is electronically isolated from the sensing electrode other than via the electrolytic medium.

A gas sensor as set forth herein has the advantage of having a very fast response time, of the order of one to two seconds or less, as well as high sensitivity, and can be made responsive to any of a number of gaseous species through selection of the sizes of pores in the gas permeable sensing electrode as well as through choice of the constitution of the electrolytic medium. Since no gas needs to dissolve in the electrolytic medium the life-time of the sensor is longer. Encapsulation is also easier. Also, additional selectivity can be provided in the passage via selective filtering. The fast response time is attained since the analyte gas passes, wholly in the gas phase, through the pores in the gas permeable electrode until it reaches the electrolytic medium. At that point the electrode, the analyte gas and the electrolytic medium are in contact with one another and the analyte is detected. Diffusion through the electrolytic medium is reduced to zero.

BRIEF DESCRIPTION OF DRAWINGS

The invention will be better understood by reference to the figures of the drawings wherein like numbers denote like parts throughout and wherein:

FIG. 1 illustrates, in side section view, a gas sensor in accordance with an embodiment of the present invention;

FIG. 2 illustrates, in plan view the embodiment of FIG. 1;

BEST MODE FOR CARRYING OUT INVENTION

Figure 3:
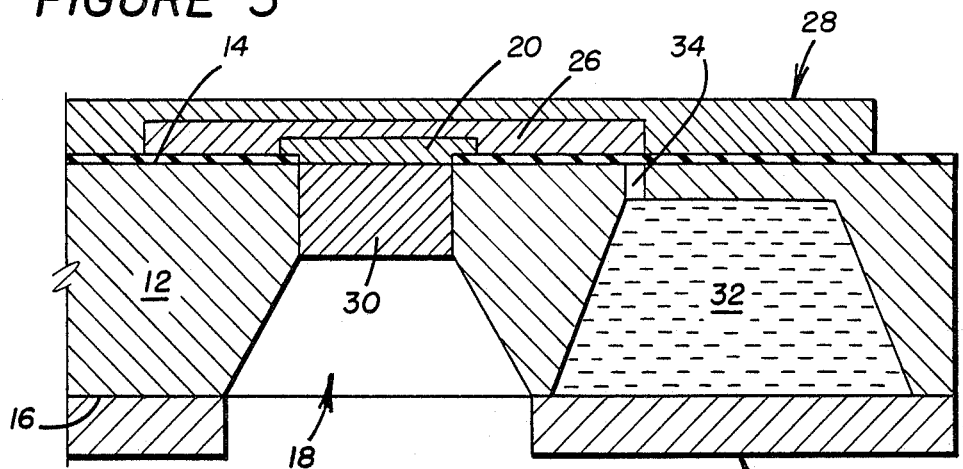
FIG. 3 illustrates, in view similar to FIG. 1, an alternate embodiment in accordance with the present invention.

FIG. 1 illustrates a gas sensor 10 in accordance with the present invention. The gas sensor 10 includes a substrate 12 having a first surface 14 and a second surface 16. In the embodiment illustrated the surfaces 14,16 face generally away from one another. A passage 18 is provided which extends through the substrate 12 from the first surface 14 to the second surface 16.

Figure 4:
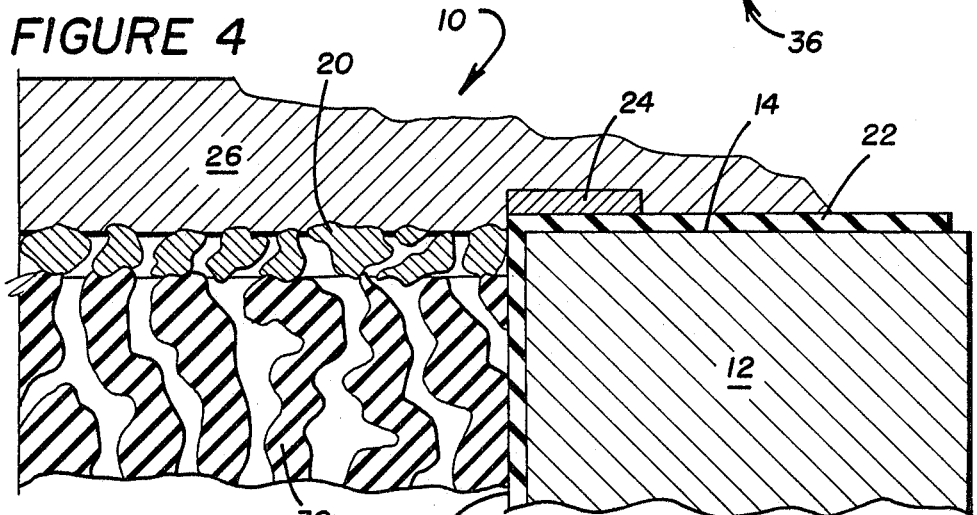
FIG. 4 illustrates, in enlarged view, in section, another alternate embodiment in accordance with the present invention.
Figure 5:
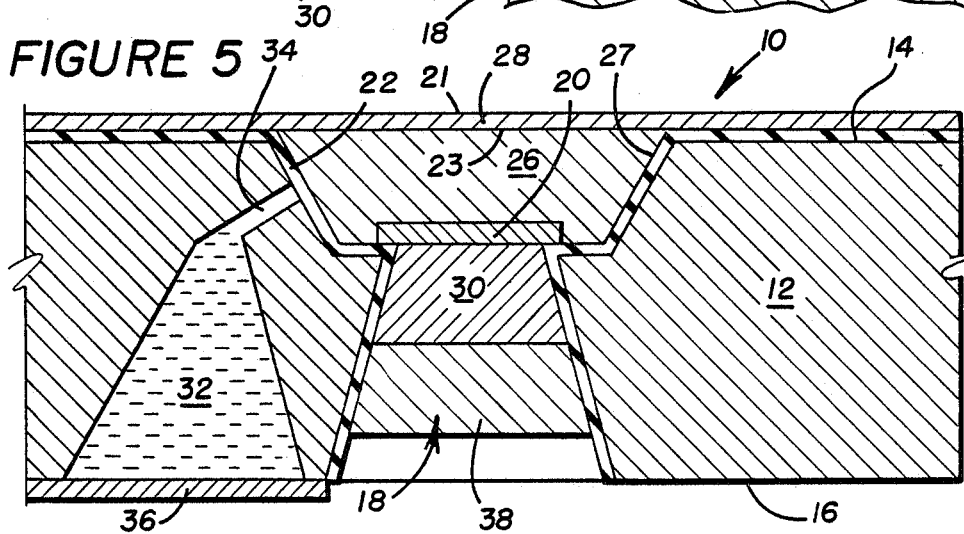
FIG. 5 illustrates, in view similar to FIG. 1, yet another alternate embodiment in accordance with the present invention.

A gas permeable sensing electrode 20 having first surface and second surface sides 21,23 is positioned across the passage 18. In the particular embodiment illustrated in FIG. 1 the gas permeable sensing electrode 20 is located on the first surface 14 of the substrate 12. However, the gas permeable sensing electrode 20 can be within the passage 18, for example, towards the first surface 14, and such is illustrated in FIGS. 4 and 5. A dielectric layer 22 can be present if the substrate 12 is a conductor or semiconductor, e.g., silicon, gallium arsenide or silicon carbide, to separate and insulate the substrate 12 from the sensing electrode 20 as well as from a counter electrode 24 seen in FIGS. 2 and 5 and, when present, a reference electrode 25 as seen in FIG. 2.

In the embodiments of FIGS. 1–4 an electrolytic medium 26 is in contact with the first surface 14, or more particularly with the dielectric layer 22, (present if the substrate 12 is a conductor or semiconductor) and with the first surface side 21 of the electrode 20 as well. In the embodiment of FIG. 5 the electrolytic medium 26 is within a front portion 27 of the passage 18, the front portion 27 being adjacent the first surface 14. The dielectric layer 22, in such embodiment, extends within the front portion 27 of the passage 18 to provide needed insulation.

Any of a number of different types of electrolytic medium 26 can be utilized. For example, the electrolytic medium 26 can be a solution, e.g., a water based solution. Alternatively, the electrolytic medium 26 can be a hydrogel. Preferable, however, particularly for voltammetric measurements, are solid electrolytes, including solid polymer electrolytes such as Nafion (a trademark of DuPont) which is part of a class of solid polymeric ion exchangers which conduct ions upon exposure to water. Probably the best known examples are membranes made from polystyrene with fixed negative sites (sulfonate, carboxylate or phosphonate) or fixed positive sites (quaternary ammonium or quaternary phosphonium). Selection as far as ions are concerned with these materials is almost exclusively on the basis of charge and for ions with the same charge discrimination is very slight. For voltammetric sensing the use of these materials is new. Other examples of solid polymeric electrolytes besides Nafion (which a is perfluorinated ionomer) are sulfonated styrene-divinyl benzene resins and divinyl napthalene sulfonic acid polymer.

Such polymers are characterized chemically and physically in that they have a hydrophobic nature with ionic (hydrophilic) clusters inside. They conduct ions upon hydration. They exclude co-ions up to the Donnan failure point at which stage ions of both types can penetrate into the resin. Neutral molecules can diffuse readily through such membranes and especially large organic molecules can dissolve within the more hydrophobic resins.

Resins can also be used as reference solutions (see, for example, French patent publication No. 2,158,905). These ion exchange resins have been used as the electrolytic medium for a potentiometric $CO_2$ sensor (see, for example, U.S. Pat. No. 3,730,868).

Useful gels for incorporation within the sensor structure include, without limitation: methylcellulose, polyvinyl alcohol, agar, carboxycellulose, gelatin, agarose, deionized gelatin, polyacrylamide, polyvinyl pyrrolidone, hydroxyethylacrylate, hydroxyethylmethacrylate, and polyacrylic acid. They are characterized in that they constitute thickened (more viscous) solutions. They are hydrophilic in natural and include synthetic polymeric film forming materials.

The electrolytic medium can alternatively be selected from a family of inorganic oxide solid proton conductors, e.g., hydrogen uranyl phosphate, protonated $\beta''$-alumina, zirconium phosphates, or antimonic acids. Other types of solid electrolytes that can conduct $O^{2-}$ ion, for example, $LaF_3$, can also be used.

Means 28 is usually provided for encapsulating the electrolytic medium 26 and the sensing electrode 20. In the embodiments illustrated the encapsulation material is simply any convenient polymer. It is generally preferred that the encapsulation material 28 be such as to be impermeable to water so that the water content of the solid polymer electrolyte remains relatively constant whereby the properties of the gas sensor 10 remain relatively constant with time. Useful encapsulating materials may be, for example Teflon membranes, silicone rubber membranes, silicon polycarbonate rubber membranes, mylar, nylon 6, polyvinyl alcohol, polyvinyl chloride, methylcellulose, cellulose acetate, high density polyethylene, polystyrene, natural rubber, fluorosilicone, dimethylsilicon rubber, any appropriate photoresist polymer, and dimethylsilicon. It is generally preferred that the membranes utilized be solution castable so as to make fabrication of the membrane more easily accomplished.

The encapsulating can be carried out by, for example, solution casting, separate casting on a different substrate and physical transfer, heat shrinking in place, solution casting utilizing an ink-jet printer, spin coating, or dip coating. If the encapsulating material is in the nature of uniform latex microspheres, made for example of polystyrene, styrene-butydiene, or Teflon (trademark of DuPont), such microspheres can be placed in position utilizing an ink-jet like technique, by dipping, by solvent spraying, or the like. If the encapsulating material is of the nature of or includes activated carbon or similar materials it can be placed in position by ink-jet type printing, solvent casting, or the like. If the encapsulating material includes, for example, other solid substance it can be placed in position similarly to the carbon particles.

Various types of sensing electrodes 20 can be used. These include, for example, electrodes 20 of platinum, platinum black, silver, gold, iridium, palladium, palladium/silver, iridum dioxide, platinum black/palladium, platinum oxide, and mixtures thereof, electronically conductive polymers, and generally any of the electrodes normally utilized in electrochemical measurements. A sensing electrode 20 will generally be chosen which is responsive to a particular gaseous species. Various conventional materials can be utilized as the counter electrode 24 and as the reference electrode 25.

The gas permeable electrode 20 can be made by deposition of metal over inert, usually polymeric, e.g., polystyrene particles (usually spheres) which later are removed leaving a gas permeable metal electrode 20 behind. The small inert particles can be removed by compressed air. Or, the gas permeable electrode 20 can be made in the manner Raney nickel is made.

A porous member 30 may be located in the passage 18 adjacent and generally in contact with the sensing electrode 20. For example, the porous member 30 may be porous silicon. Through proper formation of the porous member 30 the size of the pores can be controlled whereby the porous member 30 can be made selective for certain gases in the presence of other gases. The porous member 30 can be made, for example, by anodizing silicon in hydrofluoric acid solution at current densities between 20 and 100 $mA/cm^2$ and under illumination from an infrared filter quartz iodide lamp. The anodization leads to the silicon being permeated with a dense network of very fine pores. The pores will be preferentially oriented in a direction of current flow whereby the porous member 30 may be made preferentially gas and vapor permeable in the direction of desired gas and vapor flow. The pore diameter and the porosity of the silicon can be controlled by varying the processing parameters, particularly anodization current, hydrogen fluoride concentration and illumination.

Pores can be produced with diameters varying from 10 nanometers to 1 micrometer.

It may be desirable to provide a hydrophobic coating in the pores of the porous silicon. This can be done by silanization or dipping in a solution containing a dissolved hydrophobic coating material and vaporizing the solvent.

Other usable porous materials 30 include, for example, alumina, inorganic oxides generally, carbon, polymers, compressed inert particles, and the like.

An additional electrode, in the embodiment illustrated the counter electrode 24, is in contact with the electrolytic medium 26 and is electrically isolated from the sensing electrode 20 other than via the electrolytic medium 26. In the embodiments illustrated the dielectric layer 22 serves to separate the additional electrode 24 from the working or sensing electrode 20. The dielectric layer 22 prevents shorting via the substrate 12. The additional electrode 24 may alternatively be a reference electrode. Or, as illustrated in FIG. 2, the separate reference electrode 25 may be added to the gas sensor 10.

The substrate 12 can be made of any of a number of materials. For example, it can be made of plastic, glass, various polymers, metal oxides, semiconductors, or even metals. In the latter instances, however, it is necessary that the dielectric layer 22 be present. Preferably, the substrate 12 is made of a semiconductor material, for example silicon, silicon carbide or gallium arsenide. This allows the techniques of integrated circuit manufacturing to be utilized to form the various portions of the gas sensor 10. Furthermore, this allows the gas sensor 10 to be made very small, for example as small as 150 microns on a side and, perhaps 20 microns thick.

Note that there is the capability of providing several stages of selectivity in the gas sensor 10. First, there is a selectivity given by sizing the pores in the porous member 30, when present. Next, there is the selectivity provided by the material of the sensing electrode 20. Third there is the selectivity provided by the size of the pores in the sensing electrode 20. Furthermore, there is the selectivity provided by the selection of the composition of the electrolytic medium 26. Also, there is the selectivity provided by the selection of the materials for the additional electrode 24.

Since the gas sensor 10 of the present invention can be made very small utilizing semiconductor processing techniques, it is quite possible to construct a large number of gas sensors 10 on a single chip thus providing an array of gas sensors 10. This allows for several sensors to be made for each gas and/or for several different sensors to be made for different gases, all on a single substrate 12. Thus, high speed, selectivity and reliability can be assured.

FIGS. 3 and 5 illustrate embodiments of the present invention wherein the porous silicon includes a reservoir 32 for an aqueous liquid, generally water. A porous section 34 may be formed in the substrate 12, for example, by etching a cavity into the substrate 12 and filling it with a porous material such as the porous member 30, which will generally be silicon in this embodiment, so as to provide liquid contact between the electrolytic medium 26 and the water reservoir 32. In this manner the electrolytic medium 26 can be kept continuously hydrated to a constant extent. This increases the lifetime of the gas sensor 10. In such an instance it will generally be necessary to encapsulate the water reservoir 32 as by utilizing an encapsulating layer 36 which can be of any convenient material, for example a plastic material. Indeed, the encapsulating material 36 will generally be identical to the encapsulating means 28 used for encapsulating the electrolytic medium 26 and the sensing electrode 20. In this manner the entire encapsulation can be carried out in a single operation.

FIG. 4 illustrates an embodiment of the present invention wherein a gas permeable sensing electrode 20 is within the front portion 27 of the passage 18 and ends at the first surface 14 with the electrolytic medium 26 being external of the passage 18 on the first surface 14. In this embodiment the additional electrode 24 is in the nature of a counter electrode and is located on the dielectric layer 22 closely adjacent to the sensing electrode 20. This is done to speed up the response time of the gas sensor 10.

If desired a filter material 38 (see FIGS. 1 and 5) may be placed in the passage 18 between the second surface 16 of the substrate 12 and the porous member 30. Generally the filter material 38 is selected so as to aid in separation of gases and to thereby aid in the selectivity of the gas sensor 10. For example, the filter material 38 can be selected to selectively react with certain gas components and prevent them from reaching the porous member 30. In this manner gases which might normally pass through the porous member 30 and interfere with analysis for a selected component of a gas mixture are excludable. The filter material 38 might be in the nature of an oxidizer, e.g., potassium permanganate coated alumina particles, metal, e.g., platinum coated alumina particles, hydrophobic particles, activated carbon, gas permeable membranes, biocatalyst, e.g., an enzyme, complexing agents, e.g., EDTA, or generally any desired material which will provide selectivity of a certain gas component by excluding one or more other gas components.

FIG. 5 illustrates an embodiment of the invention wherein the sensing electrode 20 is across the passage 18 intermediate the first surface 14 and the second surface 16. Furthermore, the front portion 27 of the passage 18 is significantly expanded in size so as to permit inclusion therein of the electrolytic medium 26 and the counter electrode 24 (not shown in FIG. 5). Construction of the embodiment of FIG. 5 would generally include etching inwardly from both the first surface 14 and the second surface 16. Alternatively, laser drilling can be used. If desired, e.g., to protect the integrity of the porous member 30 and/or the filter material 38, a gas porous layer 40 may close off the passage 18 at or adjacent the second surface 16. This can provide added selectivity and/or the ability to use the sensor for dissolved gaseous species. In such an instance the gas porous layer 40 will generally be liquid (usually water) impermeable. This is useful for providing a sensor for, for example, in vivo measurement of blood gases.

The embodiment of FIG. 5, like that of FIG. 3, includes the water reservoir 32. It also uses a short sensing-counter electrode gap as does the embodiment of FIG. 4.

While in the embodiment illustrated the first surface 14 and the second surface 16 face in opposite directions it should be recognized that the invention is not so limited. For example, the first surface 14 and the second surface 16 can be non-parallel, perhaps even perpendicular. In such an instance the passage 18 is not necessarily straight throughout.

Figure 6:
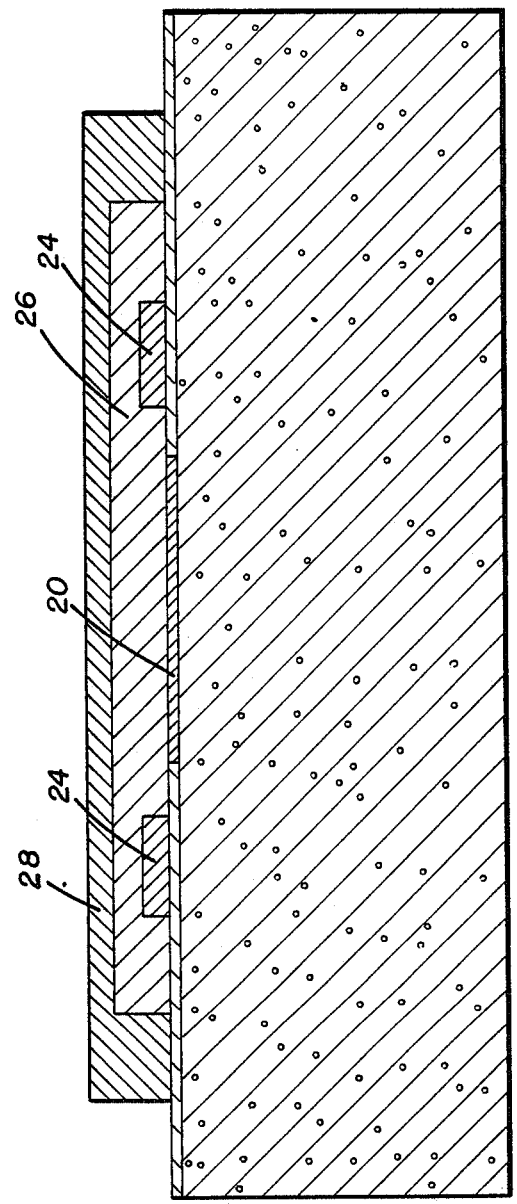
FIG. 6 illustrates, in view similar to FIG. 1, still another alternate embodiment in accordance with the present invention.

FIG. 6 illustrates an embodiment of the present invention wherein a gas sensor 110 includes a gas and vapor permeable substrate 112. In this embodiment the passage 18 can be omitted since the gases and vapors being detected can flow within the substrate 112 and thereby reach the gas permeable sensing electrode 120.

In the embodiment of FIG. 6 a first surface 114 of the substrate 112 includes means 70, in the embodiment illustrated a surface coating 72, which serves for making selected portions of the surface 114 gas and vapor impermeable while leaving an area 74 thereof which remains gas and vapor permeable.

The area or opening 74 in the coating 72 has a gas and vapor permeable sensing electrode 120 across it. The sensing electrode 120 has a front side 76 and a back side 78 with the front side 76 facing generally the same direction as does the surface 114 of the substrate 112. As mentioned, the substrate 112 itself provides a gas flow path which leads to the back side 78 of the gas vapor permeable sensing electrode 120.

An electrolytic medium 126 is in contact with the front side 114, more specifically with the coating 72 and the front side 76 of the sensing electrode 120. An additional electrode, for example a counter electrode 124, and when present, a reference electrode (not illustrated in FIG. 6) may also be in contact with the electrolytic medium 126. The additional electrode 124 is electronically isolated from the sensing electrode 120 other than via the electrolytic medium 126.

As will be noted the substrate 112, in combination with the coating 72 can be considered a substrate 112 having a surface 114 which has the opening 74 therein, that is, the coating 72 can be considered a part of the substrate 112.

One particular means 70 has been described for making selected portions of the surface 114 gas and vapor impermeable while leaving an area 74 thereof which remains gas and water permeable. That method has been the use of the coating 72 which can be deposited while blocking off portions of the first surface 114 which it is not desired to coat. Other means 70 may be utilized. For example, materials, e.g., resist materials or other polymers, may be absorbed into the top layers on and just below the surface 114 of the substrate 112, particularly on the selected portions thereof which it is desired to have gas and vapor impermeable. Or, the selected portions can be, with certain materials, for example plastics, heated and fused so as to be gas and vapor impermeable at the selected portions.

A number of materials can be utilized for the porous substrate 112. For example, it can be made of porous alumina or virtually any porous inorganic oxide. Also, porous plastic materials may be utilized. Porous conductors or semi-conductors can also be utilized but it will be necessary to provide appropriate insulating layers much as were discussed with respect to other embodiments of the present invention.

It should also be noted that additional portions of the substrate may be made gas and vapor impermeable while leaving the sensor 110 still operational. All that is necessary is that there be a gas flow path which leads through the substrate 112 to the back side 78 of the gas and vapor permeable sensing electrode 120.

INDUSTRIAL APPLICABILITY

The present invention provides a gas sensor 10 useful for analyzing any of a number of gas and/or vapor mixtures for its components. For example, the amount of oxygen in the air can be determined, as can the amount of carbon dioxide, nitrogen dioxide, hydrogen sulfide, hydrogen cyanide, nitrous oxide, nitric oxide, ozone, hydrocarbons, and the like.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A sensor for gaseous and vaporous species, comprising:
   a gas and vapor impervious substrate having first and second surfaces facing generally away from one another and having a passage through which gas can flow extending therethrough from the first surface to the second surface;
   a gas permeable sensing electrode positioned across and substantially blocking off said passage;
   an electrolytic medium in contact with said first surface and with said electrode; and
   an additional electrode in contact with said electrolytic medium via which it is in electrical contact with said sensing electrode, said additional electrode being electronically isolated from said sensing electrode other than via said electrolytic medium.

2. A sensor as set forth in claim 1, further including:
   a porous member in said passage adjacent said sensing electrode.

3. A sensor as set forth in claim 2, wherein said porous member comprises porous silicon.

4. A sensor as set forth in claim 3, wherein said porous silicon includes a hydrophobic coating in the pores thereof.

5. A sensor as set forth in claim 1, further including:
   an aqueous liquid containing reservoir in communication with said electrolytic medium.

6. A sensor as set forth in claim 1, further including:
   means for encapsulating said electrolytic medium and said sensing electrode.

7. A sensor as set forth in claim 1, wherein said substrate comprises a semiconductor material and further including a dielectric layer between said substrate and said sensing electrode, said additional electrode and said electrolytic medium.

8. A sensor as set forth in claim 1, wherein said additional electrode comprises a counter electrode.

9. A sensor as set forth in claim 8, wherein said counter electrode is positioned adjacent said sensing electrode.

10. A sensor as set forth in claim 8, further including:
    a reference electrode in contact with said electrolytic medium and electrically isolated from said sensing and counter electrodes other than via said electrolytic medium.

11. A sensor as set forth in claim 10, wherein said electrolytic medium comprises a solid polymer electrolyte.

12. A sensor as set forth in claim 11, further including:
    an aqueous liquid containing reservoir in communication with said solid polymer electrolyte.

13. A sensor as set forth in claim 10, wherein said electrolytic medium comprises a hydrogel.

14. A sensor as set forth in claim 13, further including:
an aqueous liquid containing reservoir in communication with said hydrogel.

15. A sensor for gaseous and vaporous species, comprising:
   a gas and vapor impervious substrate having a surface having an opening therein;
   a gas and vapor permeable sensing electrode having front and back sides located across and substantially blocking off said opening with said front side facing generally the same direction as does said surface;
   a gas flow path leading to said back side;
   an electrolytic medium in contact with said front side; and
   an additional electrode in contact with said electrolytic medium via which it is in electrical contact with said sensing electrode, said additional electrode being electronically isolated from said sensing electrode other than via said electrolytic medium.

16. A sensor as set forth in claim 15, further including:
an aqueous liquid containing reservoir in communication with said electrolytic medium.

17. A sensor as set forth in claim 15, further including:
means for encapsulating said electrolytic medium and said sensing electrode.

18. A sensor as set forth in claim 15, wherein said electrolytic medium comprises a solid polymer electrolyte.

19. A sensor as set forth in claim 18, further including:
an aqueous liquid containing reservoir in communication with said solid polymer electrolyte.

20. A sensor as set forth in claim 15, wherein said electrolytic medium comprises a hydrogel.

21. A sensor for gaseous and vapourous species, comprising:
   a gas and vapor permeable substrate having a surface;
   means for making selected portions of said surface gas and vapor impermeable while leaving an area thereof which remains gas and water permeable;
   a gas and vapor permeable sensing electrode having front and back sides located across and substantially blocking off said area with said front side facing generally the same direction as does said surface;
   an electrolytic medium in contact with said front side; and
   an additional electrode in contact with said electrolytic medium via which it is in electrical contact with said sensing electrode, said additional electrode being electronically isolated from said sensing electrode other than via said electrolytic medium.

22. A sensor as set forth in claim 21, further including:
an aqueous liquid containing reservoir in communication with said electrolytic medium.

23. A sensor as set forth in claim 21, further including:
means for encapsulating said electrolytic medium and said sensing electrode.

24. A sensor as set forth in claim 21, wherein said electrolytic medium comprises a solid polymer electrolyte.

* * * * *

Disclaimer 4,812,221.—*Marc J. Madou*, Palo Alto; *Takaaki Otagawa*, Fremont, both of Calif. FAST RESPONSE TIME MICROSENSORS FOR GASEOUS AND VAPOROUS SPECIES. Patent dated March 14, 1989. Disclaimer filed March 26, 1990, by the assignee, SRI International.

The term of this patent subsequent to Sept. 14, 2005, has been disclaimed.

[ *Official Gazette October 9, 1990* ]